US 7,435,864 B2

(12) United States Patent
Gershuni

(10) Patent No.: US 7,435,864 B2
(45) Date of Patent: Oct. 14, 2008

(54) METHOD AND DEVICE FOR THE PRODUCTION OF ALKYLATES

(75) Inventor: Semen Gershuni, Moscow (RU)

(73) Assignee: Orgral International Technologies Corporation, St. Michael (BB)

( * ) Notice: Subject to any disclaimer, the term of this patent is extended or adjusted under 35 U.S.C. 154(b) by 1239 days.

(21) Appl. No.: 10/297,205

(22) PCT Filed: Jun. 1, 2001

(86) PCT No.: PCT/IB01/00962

§ 371 (c)(1),
(2), (4) Date: Dec. 4, 2002

(87) PCT Pub. No.: WO01/94283

PCT Pub. Date: Dec. 13, 2001

(65) Prior Publication Data

US 2003/0158457 A1 Aug. 21, 2003

(30) Foreign Application Priority Data

Jun. 6, 2000 (CA) ................................. 2310858

(51) Int. Cl.
*C07C 2/62* (2006.01)
*B01J 8/00* (2006.01)
*B01J 19/00* (2006.01)
*B01D 12/00* (2006.01)

(52) U.S. Cl. ....................... 585/731; 585/709; 585/720; 422/224; 422/234; 422/235; 210/188; 210/189; 210/192; 210/513; 210/519; 210/521

(58) Field of Classification Search ................ 585/731, 585/719, 720; 422/224, 234, 235; 210/188, 210/189, 192, 513, 519, 521
See application file for complete search history.

(56) References Cited

U.S. PATENT DOCUMENTS 3,175,023 A * 3/1965 Gross et al. ................. 585/719

(Continued)

FOREIGN PATENT DOCUMENTS

WO WO 95/04019 A1 2/1995
WO WO 99/48845 A1 9/1999

OTHER PUBLICATIONS

Patent Abstract RU 2,131,861, Aug. 3, 1993.
Database WPI, Section Ch, Week 199822, Derwent Publications Ltd., AN 1998-249587, XP002176791, RU 2 092 475, Oct. 10, 1997.

*Primary Examiner*—Thuan Dinh Dang
(74) *Attorney, Agent, or Firm*—Foley & Lardner LLP

(57) ABSTRACT

Disclosed is a device for the production of alkylate(s) by sulfuric acid alkylation of at least one isoparaffin such as isobutane with at least one olefin, such as butylenes. The device includes a mixing chamber for preparing a mixture of the isoparaffin with recycled reaction products. It also includes an emulsion chamber for preparing a first hydrocarbons-in-sulfuric acid emulsion, where the mixture prepared in the mixing chamber is injected in multiple parallel jets into a sulfuric acid composition. The device further includes a pre-reaction chamber for preparing a second emulsion, where a given portion of the olefin is injected in jet streams into the first hydrocarbons-in-sulfuric acid emulsion coming from the emulsion chamber. Last of all, the device includes a reaction chamber of given height and cross-section where the second emulsion coming from the pre-reaction chamber is injected through nozzles and another portion of olefin is injected in jet streams all over the cross-section and height of the reaction chamber. The reaction chamber is devised so that the second emulsion is circulated in a closed circuit and it has an outlet through which a balanced amount of reaction mixture is continuously discharged. All of said mixing chamber, emulsion chamber, pre-reaction chamber and reaction chamber are coaxially arranged one above the other in vertical position and altogether form a reactor with the prechamber being located at the bottom of the reactor and the reaction chamber on top thereof. A method for the production of alkylates by means of the above device is also disclosed.

20 Claims, 4 Drawing Sheets

U.S. PATENT DOCUMENTS 3,544,652 A   12/1970   Van Dijk
5,443,799 A    8/1995   Alexanyan et al.
5,777,189 A    7/1998   Alexanyan et al.

* cited by examiner

METHOD AND DEVICE FOR THE PRODUCTION OF ALKYLATES

INVENTION BACKGROUND (a) Field of the Invention

The present invention relates to a method for the production of alkylates by sulfuric acid alkylation of isoparaffins with olefins. This method is particularly well adapted for use in the petroleum refining industry, using isobutane as isoparaffin, and butylenes as olefin.

The invention also relates to a device for mixing and reacting at least two and preferably three liquid components. This device is particularly well adapted for carrying out the above method even though it can be used for carrying out many other methods.

(b) Brief Description of the Prior Art

Alkylates are main components of high-octane motor fuels. They are produced by alkylation of isoparaffins (mainly isobutane) by olefins (such as propylene, butylenes or amylenes) in the presence of sulfuric or hydrofluoric acid that serves as a process catalyst. The most widely known method for the production of alkylates in the petroleum refining industry consists of carrying out a sulfuric acid alkylation of isobutane by olefin.

Numerous methods for carrying out sulfuric acid alkylation of isobutane by olefins are known. The method according to the invention distinguishes over most of these known method in that the reaction is carried out in a compact reactor which does not contain moving parts and in which jet mixing of the reagents is achieved.

U.S. Pat. No. 3,544,652 issued on Dec. $1^{st}$, 1970 discloses a method for the alkylation of isoparaffin by olefins in the presence of sulfuric acid, where the olefin is reacted with an alkylating hydrocarbon-in-acid emulsion formed by thoroughly mixing isoparaffin with sulfuric acid before contact with the olefin. In this patent, the isoparaffin-to-olefin volume ratio is disclosed as being equal to about 12:1. The acid-to-hydrocarbons volume ratio is disclosed as being within the range of 2.5:1 to 15:1 but it is mainly maintained at about 6:1. The reaction is carried out adiabatically, mainly in a continuous manner, in a reactor called "alkylation contactor", which is provided with a mixer that is devised for forming the isoparaffin-in-sulfuric acid emulsion and for thoroughly and homogeneously mixing the so-formed emulsion with the olefin at the points of delivery of the latter into the reactor.

As the liquid flows through the reactor, the temperature of the alkylating mixture rises continuously by 5 to 15° C., thereby reducing viscosity of the mixture and increasing its turbulence. The method is carried out at a temperature of 5 to 60° C. under a pressure sufficient for keeping the reagents in a liquid state (from 2 to 10 ATMs). Prior to being mixed with the isoparaffin, sulfuric acid at a concentration of 88 to 99% is cooled down to a temperature of about 4° C.

The emulsion preparation and the olefin injection and distribution inside the reaction area are not disclosed in detail in this U.S. patent.

The method disclosed in U.S. Pat. No. 3,544,652 is efficient but it requires a substantial amount of power for circulating the acid due to the very high acid-to-hydrocarbons ratio. It also requires a settling equipment of a very large size. Moreover, the method disclosed in this patent cannot guarantee a low consumption of sulfuric acid and a reasonably high quality of the final product.

Russian patent No. 2,131,861 granted on Jul. 25, 1994 (corresponding to U.S. Pat. Nos. 5,443,799 and 5,777,189) discloses a method for sulfuric acid alkylation of isoparaffins by olefins and a device for carrying out this method. At the initial stage of the method disclosed in this patent, a thin isoparaffin-in-sulfuric acid emulsion is made by injecting isoparaffin into an acid medium through a set of nozzles. Then the emulsion is delivered into a reaction area where olefin is fed, through a number of points normal to the emulsion flow. In this method, the alkylation is carried out under isobaric and isothermal conditions.

Russian patent No. 2,131,861 also discloses that the emulsion should preferably flow in the emulsion area at a rate of 0.2 to 2 m/s—and within the reaction area at a rate of 0.04 to 0.27 m/s. Depending on the selected flow rate, the contact between the reagents may last from a few to 60 seconds, thereby reducing to a minimum the possibility of not-wanted side reactions such as oligomerization of olefins and autoalkylation of isoparaffins. Tests have shown that this method permits to prepare a thin unstable emulsion. Separation of the reaction mixture into a hydrocarbon phase and an acid phase takes 5 to 8 seconds, thereby allowing reduction in the setting time.

Since the method described in Russian patent No. 2,131,861 does not require rotary mixers, the equipment required for carrying it out is rather cheap and of easy control and maintenance.

Russian patent No. 2,131,861 further discloses a device for carrying out the above method. This device comprises a tank for preparing the emulsion. A special appliance is provided for isoparaffin injection within the tank. Such an appliance essentially consists of a set of axially arranged nozzles. An appliance is also provided for sulfuric acid injection within the tank. The device also comprises a mixing chamber that is part of the tank, with an outlet throat, and a cylindrical reactor which is connected in line to the throat of the emulsion preparation tank. To provide olefin injection, the device comprises a perforated branch pipe extending along the axis of the reactor.

The method and device described in the above Russian patent No. 2,131,861 and its foreign counterparts have rather acceptable technical and economic parameters of operations, as proved by industrial tests. However, those parameters could be improved if use is made of a higher level of flow turbulence in the reaction zone. In practice, such a higher level of flow turbulence could be obtained if the flow rate is increased in the reaction zone and the mixing conditions of olefin and emulsion flows are improved by using a more efficient olefin feed unit instead of using a perforated branch pipe extending along the axis of the reactor.

Russian patent No. 2,092,475 granted on Dec. 6, 1995 is the closest prior art known to the Applicant. It discloses a method for the production of alkylates in a tubular reactor, which comprises mixing sulfuric acid with isobutane previously cooled down to a temperature of not over −2° C.; mixing the obtained emulsion with olefins also previously cooled to a temperature of not over −2° C., in a plurality of stages; separating the sulfuric acid from the obtained reaction mass; and recycling it. This method requests that the sulfuric acid be mixed with the isobutane and the obtained emulsion be mixed with the olefin in an injector-type mixer, with an isobutane-to-sulfuric acid injection ratio of 3.3 to 5.2 and an isobutane-to-olefin volume ratio of 3000-5000:1. In this method, sulfuric acid is separated from the reaction mass in a hydrocyclone.

Russian patent No. 2,092,475 also discloses a device for carrying out the above method, which consists of a reactor provided with three concatenated injection mixers. Each mixer is provided with an olefin injection appliance that distributes the feed in a helical fashion along the length of a device.

With the method and device disclosed in Russian patent No. 2,092,475, one may carry out sulfuric acid alkylation of isoparaffins by olefins in a compact reactor that has no moving parts. One may also obtain a high quality alkylate, as proved by industrial tests. However, in practice, an isobutane-to-olefin ratio of 3,000-5,000:1 can be obtained in the reaction area only with very high power consumption. Alkylate quality and specific sulfuric acid consumption could actually be improved by using a more efficient olefin feed unit than the perforated tube with helical openings as described in this patent. Besides, alkylate quality and specific sulfuric acid consumption could be improved by optimization of the alkylation process conditions, by proper selection of different size ratios of the reactor elements and by an improved process of separation of the reaction mixture and a device to carry out this process.

OBJECTS AND SUMMARY OF THE INVENTION

A first object of the present invention is to provide a method for the production of alkylates by sulfuric acid alkylation of isoparaffins by olefins, which has the following advantages:
reduction in power consumption;
reduction in sulfuric acid consumption; and
improvement of the alkylate quality.

In accordance with the invention, this fist object is achieved with a method for the production of alkylate(s) by sulfuric acid alkylation of at least one isoparaffin with at least one olefin, comprising the steps of:
(a) preparing a mixture of said at least one isoparaffin with recycled reaction products by mixing said at least one isoparaffin previously cooled down to a temperature lower than +12° C. with recycled reaction products separated from sulfuric acid and cooled down to a temperature lower than +12° C.;
(b) making a hydrocarbons-in-sulfuric acid emulsion by mixing sulfuric acid with the mixture obtained in step (a);
(c) preparing another emulsion by injecting a given portion of said at least one olefin in jet streams through nozzles into the hydrocarbons-in-sulfuric acid emulsion obtained in step (b);
(d) injecting the other emulsion obtained in step (c) through nozzles into a reaction chamber of given height and cross-section, where said other emulsion is circulated in a closed circuit and a corresponding amount of reaction mixture is continuously discharged;
(e) injecting another portion of the said at least one olefin in jet streams into the other emulsion through a system of injectors distributed in the reaction chamber all over the cross-section and height of said reaction chamber;
(f) processing the reaction mixture discharged from the reaction chamber through at least one hydrocyclone in order to separate said reaction mixture into an acid-containing phase and an hydrocarbon-containing phase, and subjecting each of said phases to a pressure reduction and a gas separation;
(g) recycling to step (a) one part of the hydrocarbon-containing phase that is in a liquid form after said gas separation, said recycled part acting as said recycled reaction products, recovering the remaining part of the hydrocarbon-containing phase and subjecting said recovered part to deacidification, purification and separation to extract the requested alkylate(s); and
(h) recycling to step (b) the acid-containing phase after said gas separation and a cooling, said recycled acid containing phase acting as said sulfuric acid composition, part of said acid-containing phase being withdrawn to regeneration prior to being recycled and being replaced by fresh acid.

In accordance with a preferred embodiment of the invention, the preparation of the emulsion and the alkylation process carried out in steps (a) to (d) are run in vertical flows.

In accordance with another preferred embodiment of the invention, steps (b) and (h) are controlled in such a manner that the amount of sulfuric acid circulating through the reaction chamber and processed in step (f) ranges from 40 to 80 $m^3$ per ton of commercial grade alkylate.

Preferably also, steps (b) and (d) are controlled in such a manner that in step (b), the first emulsion flows at a rate of 1.5 to 3.5 m/s and in step (d), the second emulsion flows in the reaction chamber at a rate of 2 to 4 m/s.

Further preferably, steps (c) and (d) are controlled in such a manner that said at least one olefin be injected with a pressure drop higher than 1 $kg/cm^2$.

The above method for the production of alkylate(s) by sulfuric acid alkylation of isoparaffin(s) by olefin(s) is quite efficient and ecologically safe. The number of pieces of equipment as well as the quantity of explosive, toxic and corrosive substances needed to operate the unit are dramatically reduced, such reduction being achieved not only by a lower time of reaction and a reaction chamber of smaller volume, but also by a lower time of separation of the reaction mixture in the hydrocyclone(s). Also reduced are the electric power consumption, the size required for the unit site, the man-hours, etc . . . Furthermore, the overhaul life of the device is dramatically increased, thereby resulting in a reduction in production losses. Leakage of various products in the environment is also dramatically reduced.

The method according to the invention also permits to obtain a substantial reduction in power and sulfuric acid consumption. It further permits to improve the alkylate quality.

A second object of the present invention is to provide a device that is designed, in particular, for running the process of sulfuric acid alkylation of isoparaffin by olefins. This device can also be used for carrying out a great number of other processes that require thorough mixing of several liquid components and creation of suitable conditions for their interaction.

In accordance with the invention, this second object is achieved with a device for mixing and reacting at least two liquid components, comprising:
(a) a mixing chamber for preparing a mixture of two of said components;
(b) an emulsion chamber for preparing a first emulsion, where the mixture prepared in the mixing chamber (a) is injected in multiple parallel jets;
(c) a pre-reaction chamber for preparing a second emulsion, where a given portion of one of said components is injected in jet streams into the first emulsion coming from the emulsion chamber (b); and
(d) a reaction chamber of given height and cross-section where the second emulsion coming from the pre-reaction chamber (c) is injected through nozzles and one of the components is injected in jet streams all over the cross-section and height of said reaction chamber, said reaction chamber being devised so that said second emulsion is circulated in a closed circuit and comprising an outlet through which a balanced amount of reaction mixture is continuously discharged;

wherein the mixing chamber (a), emulsion chamber (b), pre-reaction chamber (c) and reaction chamber (d) are coaxially arranged one above the other in vertical position and altogether form a reactor with the mixing chamber (a) being located at the bottom of the reactor and the reaction chamber (d) on top thereof.

When used for the production of alkylate(s), the above device more specifically comprises:
(a) mixing chamber for preparing a mixture of said at least one isoparaffin with recycled reaction products;
(b) an emulsion chamber for preparing a first hydrocarbon-in-sulfuric acid emulsion by mixing sulfuric acid with the mixture prepared in the mixing chamber (a);
(c) a pre-reaction chamber for preparing a second emulsion, where a given portion of said at least one olefin is injected in jet streams into the first hydrocarbons-in-sulfuric acid emulsion coming from the emulsion chamber (b); and
(d) a reaction chamber of given height and cross-section where the second emulsion coming from the pre-reaction chamber (c) is injected through nozzles and another portion of the at least one olefin is injected in jet streams all over the cross-section and height of the reaction chamber, wherein the mixing chamber (a), emulsion chamber (b), pre-reaction chamber (c) and reaction chamber (d) are coaxially arranged one above the other in vertical position and altogether form a reactor with the mixing chamber (a) being located at the bottom of the reactor and the reaction chamber (d) on top thereof.

A third object of the present invention is to provide a method for separating into phases the reaction mixture exiting from the above unit of sulfuric acid alkylation of at least one isoparaffin by at least one olefin, the phases including a liquid hydrocarbon-containing phase and a liquid acid-containing phase. This method has for the following advantages:
  alkylate quality improvement;
  reduction of sulfuric acid consumption;
  reduction of ethers other acid compounds in liquid reaction products; and
  reduction of acid compounds in vapor phase.

In accordance with the invention, this third object is achieved by a method which comprises the steps of:
  injecting the reaction mixture at a speed of 4 to 10 m/s into a hydrocyclone in order to separate it into a liquid hydrocarbon-containing phase and a liquid acid-containing phase; and
  further processing the phases by subjecting each of them to a pressure reduction, injecting the phase having been subjected to said pressure reduction into a gas separator, recovering liquids from said gas separator by means of a pump for further utilization, and extracting vapors from the separator by means of a compressor.

In accordance with a first preferred embodiment of the invention, each of the phases coming from the hydrocyclone and having been subjected to pressure reduction, is fed into its own separator. Part of the liquid extracted from the hydrocarbon-containing phase separator is recycled for mixing with isoparaffin in the process of alkylation of isoparaffin with olefins, as described above. The remaining part of the liquid is subjected to rectification and fractionation to extract the required alkylate. On the other hand, the main part of the liquid extracted from the acid containing phase separator is recycled and mixed with isoparaffin and the recycled reaction products to prepare the acid-to-hydrocarbon emulsion, as described above. The remaining part of the sulfuric acid-containing phase flow is withdrawn for regeneration and replaced with an appropriate amount of make-up acid.

In accordance with another preferred embodiment of the invention, the phases withdrawn from the hydrocyclone and subjected to pressure reduction are fed to a common settling vessel separated by an overflow baffle plate into a settling tank and an accumulation tank. Commercial grade products are withdrawn from the accumulation tank for rectification and extraction of the requested alkylates. Acid is withdrawn for recycling and regeneration from a lower part of the settling tank, and the reaction products to be recycled are extracted from settling tank at a level that is lower than the upper end of the overflow baffle plate of the settling vessel.

Advantageously, the hydrocarbon-containing phase can be subjected to another separation in additional hydrocylone. After reduction and vapor extraction, the upper lightweight flow from the additional hydrocyclone can be subjected to rectification and fractionation to extract the requested commercial grade alkylate while the lower heavy weight flow after vapor extraction can be recycled to the reactor.

Advantageously also, the acid-containing phase can be subjected to another separation in another additional hydrocyclone. The upper lightweight flow extracted from the additional hydrocyclone can be recycled while the lower heavy weight flow can be separated in yet another additional hydrocyclone. The lower heavy weight flow from the last hydrocyclone can be used as a second portion of acid to be recycled to the reactor while the upper lightweight flow can be withdrawn for regeneration.

A fourth and last object of the present invention is to provide a device that is designed, in particular, for separation of the reaction mixture of the unit of sulfuric acid alkylation of isoparaffins by olefins into liquid acid-containing and hydrocarbon-containing phases and a vapor phase. This device can be also used as a 3- or 4-phase separator in processes where vapor phase is withdrawn by a single flow while liquid phases are withdrawn in three separate flows. This device can be used, for example, as a 3-phase separator for the treatment of gas-saturated and water containing oil where casing-head gas is withdrawn by a single flow while oil and water are withdrawn by three separate flows. For example, dry oil can be withdrawn by a single flow while water can be withdrawn by two separate flows. One flow is directed to after purification and subsequent pumping in an oil bed or pond discharge wherein another flow is directed to the head of the process for system recycling as a heat carrier or demineralizing agent.

In accordance with the invention, this fourth object is achieved with a device for separating a reaction mixture containing immiscible liquids of different densities and free gas or vapor, in such a manner as to obtain no less than three liquid flows and at least one gas or vapor flow. This device comprises a horizontal vessel incorporating:
(a) at least one vertical overflow baffle plate that extends within said vessel and divides it into one settling tank and at least one accumulation tank;
(b) supply connecting pipes for introducing the reaction mixture into the settling tank;
(c) outlet connecting pipes for discharging the acid-containing phase from a bottom portion of the settling tank;
(d) other outlet connecting pipes for discharging the liquid hydrocarbon phase in the form of two separate flows, one of said flows being directed back to the unit for use as recycled reaction products, the other one of said flows consisting of commercial grade reaction products and being subjected to rectification and fractionation in order to obtain commercial grade alkylates, wherein the other outlet connecting pipes through which the other one of the flows exits from the vessel is located in a bottom portion of said at least one accumulation tank; and (e) at least one further outlet connecting pipes for discharging the vapor phase from an upper part of the vessel.

In accordance with a first preferred embodiment of the invention, the connecting pipes used for withdrawal of the reaction products to be recycled is in the form of a perforated pipe header extending in the settling tank at a given distance from the baffle plate, said pipe header having an axis parallel to the overflow baffle plate and extending upwards at a given height from the bottom portion of said settling tank.

In accordance with another preferred embodiment of the invention, the vessel comprises two overflow baffle plates that divide the vessel into one settling tank and two accumulating tanks. One of the accumulating tanks is used for collecting the commercial grade reaction products and the other accumulating tank is used for collecting the recycled reaction products. The settling tank can also be divided by another baffle plate of a given height into two settling sections for collecting commercial grade products and recycled reaction products, respectively.

The invention and its advantages will be better understood upon reading the following non-restrictive description of preferred embodiments thereof made with reference to the accompanying drawings.

Figure 1:
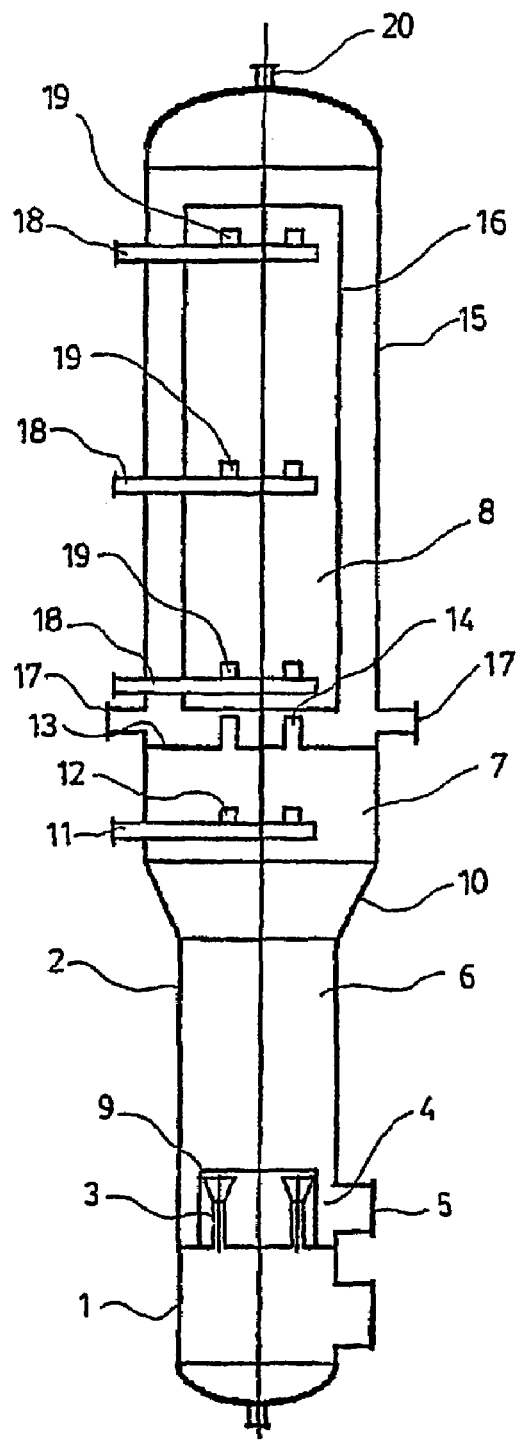
FIG. 1 is a schematic representation of a device for the production of alkylate(s) according to a preferred embodiment of the invention.

It is worth noting that the dimensions and relative proportions of each of the components of the device and units shown in the accompanying drawings do not reflect the invention as it can be reduced to practice. By way of example, the hydrocyclone(s) shown in FIGS. 2 and 3 may be, in practice, 2 to 4 times larger in size than the device per se. Also shown in a simplified way are the elements of the emulsion chamber of the reactor and of a unit for the introduction of sulfuric acid into said emulsion chamber. However, such dimensions and proportions are not essential and are actually obvious for any one who would manufacture the device or alkylation unit according to the invention.

It is worth noting also that the same reference numerals have been used throughout the following description to identify the same structural elements, whatever be the illustrated embodiment.

DESCRIPTION OF THE PREFERRED EMBODIMENT

The device according to the preferred embodiment of the invention as shown in FIG. 1 includes the following basic units:

a mixing chamber 1 for mixing isoparaffin with recycled reaction products;

an emulsion chamber 2 comprising a peripheral annular space 4 with a pipe connection 5 for introduction of a sulfuric acid composition, a mixing area 6, and a system of inlet branch pipes 3 that are parallel to the chamber axis and are designed for injection of the mixture coming from the mixing chamber, each pipe 3 being provided with a bell mouth at the outlet;

a pre-reaction chamber 7; and a reaction chamber 8.

The units are concatenated as shown in FIG. 1, and they altogether form an adiabatic reactor that can be used for sulfuric acid alkylation of isoparaffin by olefins with jet mixing of the components.

As is shown, all the chambers of the device are coaxial and installed vertically in their operative position with the mixing chamber 1 in the lower part of the device and the reaction chamber 8 on top of it.

The emulsion chamber 2 includes a centrally positioned cylindrical socket 9 which defines the peripheral annular space 4. The emulsion chamber has a height equal to 20 to 60 times the internal diameter of the inlet branch pipes 3 used for the hydrocarbon mixture injection. An enlargement fitting 10 is joined to the outlet of the chamber 2.

The pre-reaction chamber 7 extends in line on top of the enlargement fitting 10. An olefin feed injection unit 11 is provided at the bottom of the pre-reaction chamber 7. This injection unit comprises injectors 12 having their axes running upward at an angle of 0 to 30° with respect to the vertical.

The reaction chamber 8 is separated from the pre-reaction chamber 7 by means of a baffle 13 having nozzles 14 mounted therein for providing passage to the reaction mixture. It comprises a vertical housing 15 and a circulation pipe 16 which is coaxial with the housing and installed with side clearances relative to the housing to allow recirculation of the injected emulsion in a closed circuit. Several connecting pipes 17 are tied into the bottom of the housing 15 of the reaction chamber 8 for withdrawal of the reaction mixture.

Injectors 19 connected to supply pipes 18 are provided for injecting an olefin feed near the top and bottom ends of the circulation pipe 16 and in one or several tiers over the pipe height. These injectors 19 have their axes running upward at an angle of 0 to 30° with respect to the vertical. Preferably, each tier provided along the height of the circulation pipe 16 comprises at least three injectors 19.

The nozzles 14 mounted in the baffle 13 separating the pre-reaction chamber from the reaction chamber are arranged along a circle whose diameter is equal to 0.6 to 0.75 times the inner diameter of the circulation pipe 16. The inner diameter of the circulation pipe 16 is equal to 0.55 to 0.75 times the inner diameter of the housing 15 of the reaction chamber.

The height of the circulation pipe is preferably equal to 3 to 9 times its inner diameter. Preferably also, the sum of the cross-sections of the nozzles 14 of the baffle 13 is equal to 0.04 to 0.2 times the cross-section of the circulation pipe.

Advantageously, the reaction chamber 8 is also provided with an additional axial connecting outlet 20 on its top to allow liquid or vapor emission directly from the reaction chamber whenever required during regular operation of the reactor and/or during preparatory and final operations for reactor start-up and shut-down.

Figure 2:
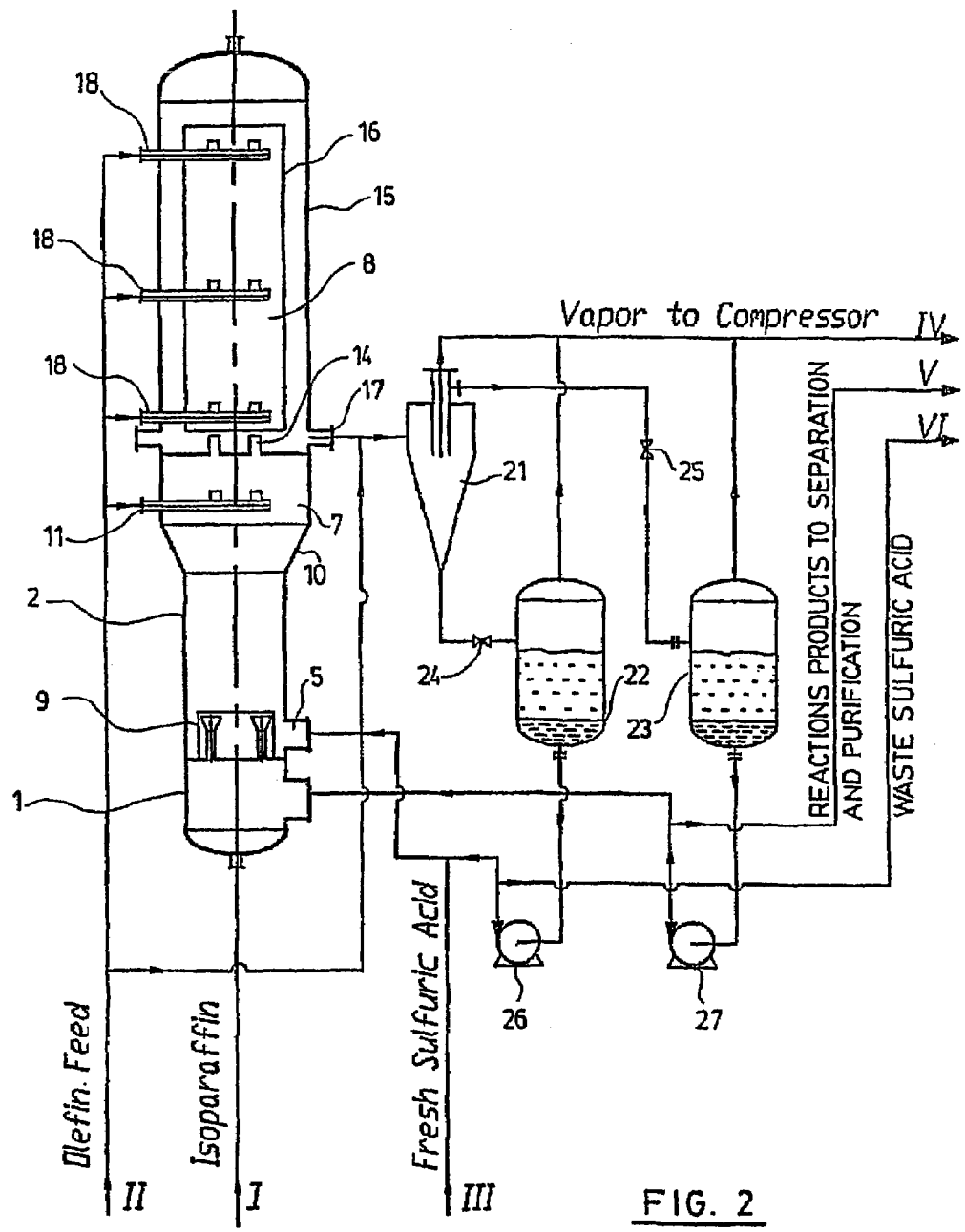
FIG. 2 is a schematic representation of an alkylation unit incorporating the device shown in FIG. 1.

FIG. 2 is a simplified flow chart of an example of alkylation unit in which incorporating the device according to the preferred embodiment invention as shown in FIG. 1 can be incorporated.

As can be seen, the unit shown in FIG. 2 incorporates the device shown in FIG. 1, a hydrocyclone 21 connected to the connecting pipes 17 and injectors 19 of the reaction chamber 8, an acid gas separator 22 and a hydrocarbon gas separator 23 connected to the hydrocyclone 21, a set of pressure reducing valve 24 and 25 respectively connected to the gas separators 22 and 23 upstream of the same, and a set of pumps 26 and 27 respectively connected to the gas separators downstream of the same.

In use, the isoparaffin used as starting material is cooled down to a temperature lower than +12° C. The so called isoparaffin is fed via a line I into the mixing chamber 1 of the device where recycled reaction products cooled down at a temperature lower than +12° C. are simultaneously injected by the pump 27. The mixture obtained in the chamber 1 is fed in multiple parallel jets through the inlet branch pipes 3 into the emulsion chamber 2 where sulfuric acid is also fed. The jets are directed through the pipe connection 5 into the peripheral annular space 4 of the emulsion chamber 2. The fine-dispersed emulsion formed in the emulsion chamber 2, exits from the same through the enlargement fitting 10. A given portion of the olefin supplied by the olefin feed injection unit 11 is fed through the nozzles 12 in the emulsion to react with the isoparaffin contained in it. Such a reaction occurs in the pre-reaction chamber 7. The second emulsion which is so formed, is fed through the nozzles 14 into the reaction chamber 8 where it is circulated in a closed circuit by means of the circulating pipe 16, the housing 15, the baffle 13 and the upper end of the reactor. A balanced amount of the reaction mixture formed within the reaction chamber 8 is withdrawn through the connecting pipe 17. In several tiers over the height of the reaction chamber, near the inlet and outlet ends of the circulation pipe 16 as well as near the middle part of its height, another portion of the olefin feed is injected in jet streams into the emulsion through the supply pipes 18 and injectors 19. A further portion of the olefin feed also can be injected into the reaction chamber at the outlet of the same.

The reaction mixture exiting the reaction chamber 8 is fed into the hydrocyclone 21 where it is separated into a heavy weight, acid-containing phase and a light weight, hydrocarbon-containing phase. Instead of one hydrocyclone as shown in FIG. 2, use could be made of a set of hydrocyclones that would include several concatenated hydrocyclones per each phase to be extracted in order to provide a required level of rectification of every such phase. Such will be better disclosed hereinafter with reference to FIG. 3 and FIG. 4.

In use, vapor may be liberated in the hydrocyclone. Therefore, the hydrocyclone is preferably designed in order to provide a vapor exit via a separate line IV leading to a compressor (not shown). The separated acid-containing phase is withdrawn from the bottom of the hydrocyclone 21 and fed into the gas separator 22 via a pressure reducing valve 24. As a result of throttling in the valve, a given amount of hydrocarbons contained in the acid is boiled away, thereby cooling off the acid. Vapor formed by boiling is withdrawn from the separator 22 and directed to a compressor (not shown) via the line IV while the pump 26 recycles the cooled sulfuric acid composition into the emulsion chamber 2. A given amount of waste acid may be withdrawn for regeneration via a line VI. A corresponding amount of fresh acid may then be fed via a line III to compensate it The light weight, hydrocarbon-containing phase is fed from the hydrocyclone through a reducing valve 25 into another gas separator 23 where vapor separated as a result of throttling is also directed to the compressor (not shown) via the line. The reaction products cooled due to evaporation of their most easily boiling components, are separated into two parts. One part is recycled into the mixing chamber 1 by the pump 27 (as recirculated reaction products), while the other part is fed via a line V to an adjacent neutralization, rectification and separation unit (not shown) for the purpose of obtaining the requested base product—alkylate.

Tests carried out by the Applicant have shown that best results are achieved when the amount of sulfuric acid circulating through the device according to the invention and of the other components of the alkylation unit that are used for separation of the recycled reaction mixture ranges between 40 to 80 m$^3$/t of commercial grade alkylate.

Best results are also achieved when the first emulsion flows at a speed of 1.5 to 3.5 m/s and the second emulsion at a speed of 2 to 4 m/s within the device.

Best results are further achieved when the pressure drop at the level of the nozzles 12 and 19 connected to the olefin feed injection unit 11 and to the supply pipes 18 is higher than 1 kg/cm$^2$, and preferably between 1 and 4 kg/cm$^2$.

Best results are still further achieved when the reaction mixture is introduced into the hydrocyclone 21 at a speed of 4 to 10 m/s.

Advantageously, sensors (not shown) connected to a control panel may be provided to check all these parameters and ensure that they fall within the above mentioned ranges.

Figure 3:
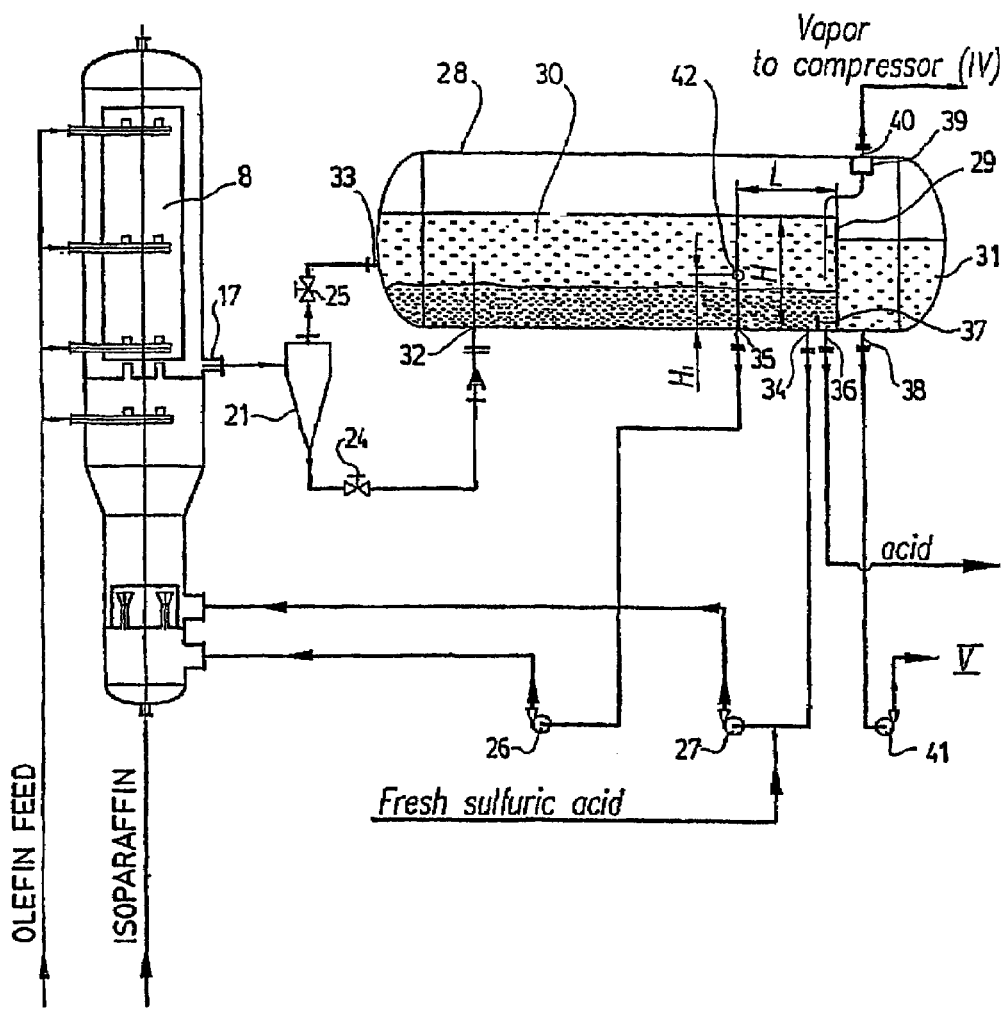
FIG. 3 is a schematic representation of another alkylation unit incorporating the device shown in FIG. 1 and a device for separating the obtained products.

FIG. 3 is a flow chart of another example of an alkylation unit incorporating the device according to the preferred embodiment of the invention as shown in FIG. 1.

The unit shown in FIG. 3 comprises the device shown in FIG. 1. The unit also comprises a hydrocyclone 21 connected to the outlet connecting pipe 17 of the reaction chamber 8 to separate the reaction mixture into a hydrocarbon-containing phase and an acid-containing phase. The unit further comprises a gas separator 28 for removing gas and vapor from the hydrocarbon-containing and acid-containing phases after the same have been subjected to a pressure reduction through a set of valves 24 and 25. The unit still further comprises pumps 26 and 27 for recycling the reaction products and acid.

The gas separator 28 consists of a horizontal vessel that is divided by a vertical baffle plate 29 into a settling tank 30 and an accumulation tank 31. The setting tank 30 is provided with supply connecting pipes 32 and 33 connected to the valves 24 and 25, respectively, through which the acid-containing and hydrocarbon-containing phases are separately fed. The settling tank is also provided with outlet connecting pipes 34 and 35 through which the settled acid and reaction products to be recycled may be extracted. These connecting pipes are connected to the pumps 26 and 27 for recirculation of the reaction products and acid. The gas separator 28 also comprises a separate connecting pipe 36 for discharge of spent acid for regeneration. This connecting pipe 36 opens into a compartment formed at the bottom of the settling tank between the overflow baffle plate 29 and an additional baffle 37 provided at the bottom of the settling tank upstream the baffle plate 29. Such an arrangement allows discharge of a lighter acid-containing phase.

Another outlet connecting pipe 38 is provided in the lower part of the accumulating tank 31 for allowing withdrawal of liquid reaction products in liquid form. This connecting pipe 38 is connected to a pump 41 which discharges the reaction products for rectification and deisobutanization in order to extract the requested commercial grade alkylate. As shown, the upper part of the accumulation tank 31 is provided with a knockout drum 39 and a further outlet socket 40 for vapor withdrawal to a compressor.

Advantageously, the unit shown in FIG. 3 may also comprise another outlet connecting pipe positioned to allow withdrawal of the reaction products for recycling purpose from a level that is lower than the height of overflow baffle plate. This connecting pipe 42 can be in the form of an horizontal perforated pipe header or collector having an axis parallel to the overflow baffle plate 29 and a height measured from a bottom portion of the vessel 28 that is equal to $H_1$. $H_1$ is preferably 0.5 to 0.8 time the height H of the overflow baffle plate. The header or collector 42 is located at a distance L from the baffle plate, that is preferably equal to 0.25 to 1.0 time the height H of said baffle plate.

Figure 4:
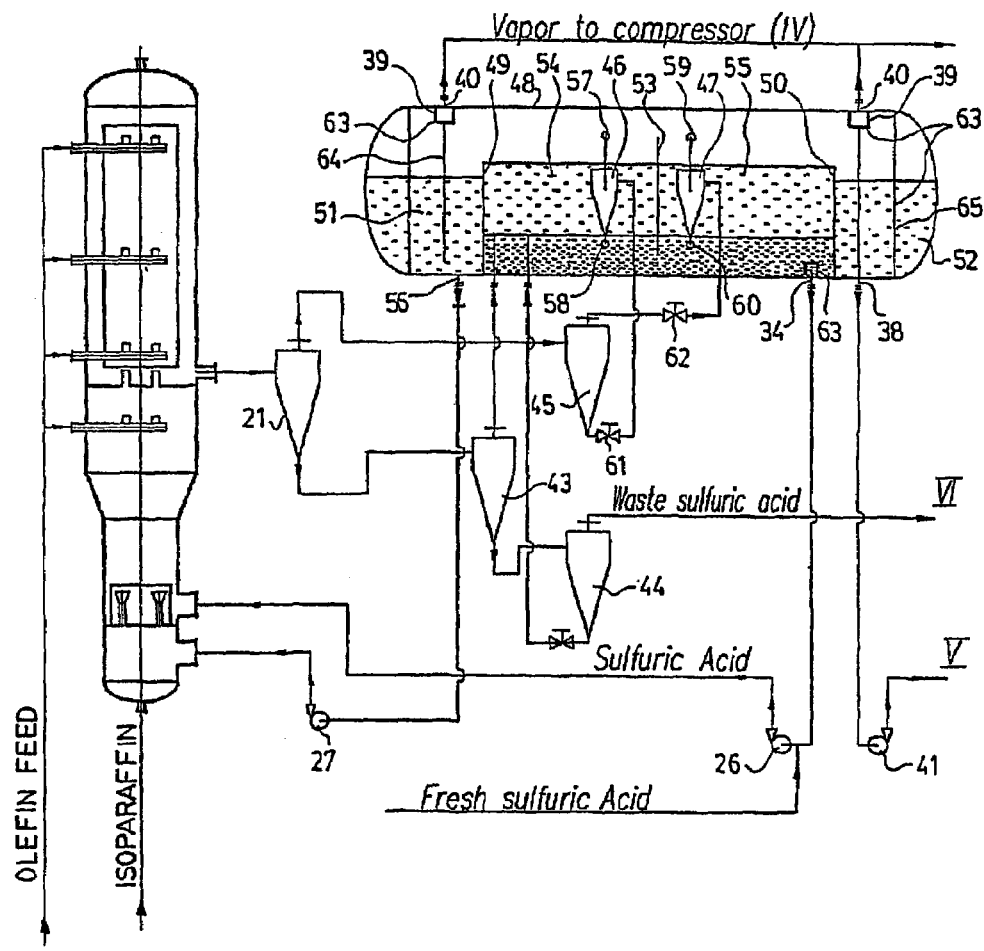
FIG. 4 is schematic representation of a further alkylation unit incorporating the device shown in FIG. 1 and another device for separating the obtained products.

FIG. 4 is a flow chart of a further example of an alkylation unit incorporating the device according to the preferred embodiment of the invention as shown in FIG. 1.

The unit shown in FIG. 4 comprises the device shown in FIG. 1. It also comprises a hydrocyclone 21 connected to the outlet connecting pipe 17 of the reaction chamber 8. It further comprises two other hydrocyclones 43 and 44 for sharp separation of the acid-containing phase separated within the hydrocylone 21, and one further hydrocyclone 45 for sharp separation of the hydrocarbon-containing phase separated within the hydrocyclone 21. The unit also comprises a cyclone gas separator 46 for processing the heavy weight lower flow discharged from the hydrocyclone 45, a cyclone gas separator 47 for processing the lightweight upper flow discharged from the hydrocyclone 45, and a separator 48.

The separator 48 consists of an horizontal vessel that is separated by a set of baffle plates 49, 50 into two opposite liquid hydrocarbons accumulating tanks 51 and 52 and a central settling tank. The settling tank that is formed between the baffles 49 and 50, is also divided by a vertical baffle 53 into a settling section 54 for the reaction products to be recycled, and a settling section 55 for the commercial grade reaction products to be recovered. The lower end of the baffle 53 extends at a distance away from the bottom of the vessel 48 while its upper end extends at 30 to 100 mm above the upper ends of the baffles 49 and 50. The bottom portion of the accumulating tank 51 is provided with a connecting pipe 56 for discharge of the reaction products to be recycled while the bottom portion of the accumulating tank 52 is provided with a connecting pipe 38 for discharge of the commercial grade reaction products.

The setting section 54 for the reaction products to be recycled is connected by means of outlet connecting pipes 57, 58 to the cyclone gas separator 46. As shown, the outlet connecting pipe 57 that is used for vapor discharge from the separator 46 extends higher than the upper end of the baffle 49. As also shown, the connecting pipe 58 used for extraction of the liquids from cyclone gas separator 46, extends in the lower part of the separator 48.

The settling section 55 for the commercial grade reaction products to be recovered is connected by means of outlet connecting pipes to the cyclone gas separator 47. As shown, the outlet connecting pipe 59 that is used for vapor discharge from the separator 47 extends higher than the upper end of the baffle 50. As also shown, the connecting pipe 60 used for extraction of the liquids from the cyclone gas separator 47 extends in the lower part of the settler 48.

As may be seen, the separators 46 and 47 are connected to the corresponding outlets of the hydrocyclone 45 through a pair of pressure reduction valves 61 and 62.

A connecting pipe 34 is provided at the bottom of the settling section 55 for discharging the acid to be recycled. A vortex breaker 63 is mounted above the connecting pipe 34 to exclude funnel formation and hydrocarbon suction into the acid to be recycled. The upper part of each accumulating tank is also provided with a knockout drum 39 and a connecting pipe 40 for vapor discharge to a compressor. Each knockout drum 39 is provided with a bottom 63 from which projects a downcomer leg 64, 65 having a lower open end dropping into the lower part of the corresponding accumulating tank, The method that may be carried out with the unit shown in FIG. 3 is generally similar to the one described earlier. The main difference is that after discharge from the hydrocyclone 21 and pressure reduction through the valves 24 and 25, the acid-containing and hydrocarbon-containing phases obtained from the reaction mixture are fed in the gas separator 28 for complete mixture separation. The separated vapor is discharged to a compressor through the knockout drum 39 and connecting pipe 40. A downcomer leg projecting beneath the liquid level of the settling tank trickles down the liquid separated in the knockout drum. In this settling tank, parallel flows of acid and liquid hydrocarbons provides further rectification due to their density difference. An acid cooling is also achieved since the layer of reaction products which is cooler than the layer of acid, is located above the layer of acid. As proved by results of tests carried out by the Applicant, the acid temperature at the inlet of the gas separator is 2-3° C. higher than the temperature of the hydrocarbons that have been cooled down. Such is due to partly evaporation of isoparaffins by pressure reduction. To sum up, heat exchange efficiency is very high due to following reasons:

direct contact of mediums with different temperatures;
constant renewal of contact surface due to emergence and evaporation of reaction products obtaining heat from a warmer acid located beneath;
sinking of acid globules cooled at the contact surface and replacement thereof with warmer globules emerging from the bottom.

The reaction products to be recycled are directed by the pump 26 back to the mixing chamber 1 through the perforated collector 42 and the connecting pipe 35. The remaining amount of reaction products flows over the baffle plate into the accumulation tank 31, from which they are discharged by the pump 41 through the connecting pipe 38 towards a rectification and deisobutanization unit (not shown) in order to obtain the requested commercial grade alkylate.

The sulfuric acid to be recycled is withdrawn from the bottom part of the vessel 28 via the connecting pipe 34 and is pumped back for recycling by the pump 27 as it was described earlier.

As shown in FIG. 3, withdrawal of spent acid for regeneration is provided via the connecting pipe 36 connected to the compartment formed between the overflow baffle plate 29 and the additional baffle 37. Such allows withdrawal of a lighter phase of the reaction mixture to regeneration.

The alkylation unit shown in FIG. 3 permits to produce a high quality, commercial grade alkylate and to reduce the sulfuric acid consumption due to a rapid emulsion separation in the hydrocyclone, an efficient cooling of the acid in the gas separator and an efficient after-settling process of the commercial grade reaction products that provides minimum carry-over of acid particles to the accumulating and roll-out areas.

However, the way of carrying out the method according to the invention is not limited to the flow chart given as example only in FIG. 3. As a matter of fact, FIG. 4 shows another possible way of carrying out the method according to the invention for sulfuric acid alkylation of isoparaffins by olefins.

Like in the examples shown in FIGS. 2 and 3, the hydrocyclone 21 of the unit shown in FIG. 4 is used to separate the reaction mixture into a hydrocarbon-containing phase and an acid-containing phase. Such a separation suspends further chemical conversion in the emulsion and sets the composition of the reaction products. However, unlike the earlier examples, the hydrocarbon-containing phase separated within the hydrocyclone 21 is subjected to another separation into an upper lightweight flow and a bottom heavy weight flow within the other hydrocyclone 45 that is located downstream. The upper lightweight flow exiting from the upper outlet of the hydrocyclone 45 qualifies as commercial grade reaction products and is fed via the pressure reduction valve 62 and the gas separator 47, to the settling section 55 of the vessel 48. The vapor phase at the upper outlet of the gas separator 47 exits above the level of the overflow baffle plate 50 that determines the liquid level in the vessel. The liquid phase separated within the gas separator 47 exits from the same below that level, e.g. beneath the liquid layer. The bottom heavy weight flow exiting from the bottom outlet of the hydrocyclone 45 forms the reaction products to be recycled and is fed via the pressure reduction valve 61 and the gas separator 46 to the other settling section 54 of the vessel 48. Vapor and liquid phases exiting the gas separator 46 are fed into the section 54 at heights similar to what has been described earlier.

The acid-containing phase collected at the bottom of the hydrocyclone 21 is separated within the hydrocyclone 43 into an upper lightweight flow and a bottom heavy weight flow. The upper flow that is enriched by hydrocarbons is fed to the settling tank of the vessel 48, preferably to the settling section 54, as reaction products to be recycled. The bottom heavy weight flow exiting from the hydrocyclone 43 is fed to a further hydrocyclone, viz. the one numbered 44, for further separation. The heavy weight layer exiting from the bottom of hydrocyclone 44 is fed to the settling section 54 of the vessel 48 for further utilization as recycled acid, along with the upper lightweight flow exiting from the hydrocyclone 43. The upper lightweight flow exiting from the hydrocyclone 44 is discharged from the unit as waste acid.

Several settling areas are formed within the vessel 48. The vapor flows are collected above the level of the overflow baffle plates 49 and 50. Some of these vapors come from the gas separators 46 and 47. Other vapors come from isobutane evaporation in the settling sections 54 and 55 due to the heat exchange between the hydrocarbons and the lower warmer layer of acid. All these vapors are withdrawn via the knockout drums 39 and connecting pipes 40 located above each of the accumulating tanks 51 and 52. The vapors are then directed to a compressor for compression, condensation, cooling and return to recycling as one of the portions of recycled isobutane. Reaction products to be recycled are collected in the settling tank 54 formed between the baffles 49 and 53. As the level of baffle 49 is 30 to 100 mm lower than the level of baffle 53, the reaction products that reach the top edge of the baffle 49, spill over it into the accumulating tank 51, from where they are pumped via the connecting pipe 56 and the pump 27 back to the reactor. Prior to reaching the settling section 55, the liquid reaction products fed therein are subjected to a two-stage acid separation in the hydrocyclones 21 and 45. Therefore, they practically do not contain any more acid particles. Thus, upon spilling over the baffle 50 into the accumulating tank 52, they can be pumped via the connecting pipe 38 and pump 41 for further treatment, where they require significantly less rectification efforts.

Sulfuric acid which forms the heaviest flow, is collected in the bottom part of the vessel 48. The so collected acid is completely decontaminated (degased) and cooled. The acid may freely flow under the baffle 53 since the bottom end of this baffle 53 is spaced apart from the bottom of the vessel. In the embodiment shown in FIG. 4, heat exchange between the acid and hydrocarbons is intensified due to the introduction of the acid into the layer of hydrocarbons and vice versa. In the embodiment shown in FIG. 4, acid is also withdrawn via the hood 63 with a crosspiece mounted over the connecting pipe 34. This feature eliminates funnel formation and suction by acid flow, of hydrocarbons located under the acid layer.

EXAMPLE

Tests to check the efficiency of the method according to the invention were carried out in a pilot unit having a structure similar to the one shown in FIG. 3 and the following particulars:

| | |
|---|---|
| diameter of the emulsion chamber 2: | 300 mm |
| diameter of the reaction chamber 15: | 700 mm |
| number of nozzles 12: | 3 |
| number of nozzles 19: | 9 |
| amount of $H_2SO_4$ circulated through the device: | 50 m³/per ton of alkylate |
| first emulsion flow rate: | 2.55 m/s |
| second emulsion flow rate: | 3.6 m/s |
| olefin injection pressure drop: | 2.5 kg-force/cm² |

During the tests, isobutane was fed into the device after having been cooled down to a temperature of +3.8° C. Recycled reaction products were also fed into the device after having been separated from the sulfuric acid and then cooled down to a temperature of +3.2° C. A mixture of hydrocarbons was fed to the emulsion chamber of the reactor in multiple parallel jets. Sulfuric acid circulating in the system and separated from the reaction products was fed in the peripheral annular space of the reactor beneath the diffuser of the emulsion chamber. Then, 27% of the total olefin feed was injected in wakes through the nozzles 12 into so prepared emulsion of hydrocarbons in sulfuric acid. The olefin feed represented a mixture of incoming butane-butylenes fraction and some part of internally recycled isobutane. The composition of the olefin feed was as follows:

| components | $C_3H_8$ | $C_3H_6$ | i-$C_4H_{10}$ | n-$C_4H_{10}$ | $\Sigma C_4H_8$ | i-$C_5H_{12}$ | rest of the components |
|---|---|---|---|---|---|---|---|
| % vol. | 1.1 | 0.1 | 74.3 | 8.3 | 15.9 | 0.2 | 0.1 |

An interaction process of olefins (essentially butylenes) contained in the feed with isobutane took place in the pre-reaction chamber 7 above the nozzles 12. Such a process was also continued through the nozzles 14 mounted on the baffle that separates the pre-reaction chamber 7 from the reaction chamber 8.

The injectors 19 for the injection of the balance of the olefin feed were arranged below the low end of the circulation pipe 16 and in two tiers over its height. All the balance of the feed was injected through the injectors 19 into the emulsion. The so-obtained reaction mixture was removed from the reactor through three connecting pipes located at the bottom part of the reaction chamber, and it was directed to the hydrocyclone 21 for separation. The reaction mixture temperature at the outlet of the reactor was +6.5° C. Initial separation of the reaction mixture from the reactor was provided in the hydrocyclone at a rate at supply pipe of 4.7 m/s. Final separation after pressure reduction was obtained in the horizontal separator vessel divided into one settling tank and one accumulating tank.

After separation, part of the reaction products was directed for an acid and alkali wash with a further isolation of alkylate while the other part was recycled through the device.

After separation from the hydrocarbons and cooling, the acid was recycled in the unit with a discharge of part of the waste acid and a replenishment of a make-up (fresh) acid, in such a way that the average strength of the recycled acid mixture was maintained at 91-92%.

The so obtained alkylate has the following characteristics:

| Results of ASTM D-86 single stage laboratory distillation | | | | | | |
|---|---|---|---|---|---|---|
| | | Boil-off | | | | |
| | Initial boiling | 10% | 50% | 90% | End boiling | MON |
| Temperature in ° C. | 37 | 64 | 108 | 149 | 195 | 93* |

*octane number

Of course, numerous modifications could be made to the device and units disclosed hereinafter without departing from the scope of the invention.

The invention claimed is:

1. A method for the production of alkylate(s) by sulfuric acid alkylation of at least one isoparaffin with at least one olefin, comprising the steps of:
    (a) preparing a mixture of said at least one isoparaffin with recycled reaction products by mixing said at least one isoparaffin previously cooled down to a temperature equal to or lower than +12° C. with recycled reaction products separated from sulfuric acid and cooled down to a temperature equal to or lower than +12° C.;
    (b) preparing a first hydrocarbons-in-sulfuric acid emulsion by injecting the mixture obtained in step (a) in multiple parallel jets into a sulfuric acid composition;
    (c) preparing a second emulsion by injecting a given portion of said at least one olefin in jet streams through nozzles into the first hydrocarbons-in-sulfuric acid emulsion obtained in step (b);
    (d) injecting the second emulsion obtained in step (c) through nozzles into a reaction chamber of given height and cross-section, where said second emulsion is circulated in a closed circuit and a balanced amount of reaction mixture is continuously discharged;
    (e) injecting another portion of said at least one olefin in jet streams through a system of injectors into the second emulsion circulating into the reaction chamber, all over the cross-section and height of said reaction chamber;
    (f) processing the reaction mixture discharged from the reaction chamber through at least one hydrocyclone in order to separate said reaction mixture into an acid-containing phase and a hydrocarbon-containing phase and subjecting each of said phases to a pressure reduction and a gas separation;
    (g) recycling to step (a) one part the hydrocarbon-containing phase that is in a liquid from after said gas separation, said recycled phase acting as said recycled reaction products, recovering the remaining part of said hydrocarbon-containing phase and subjecting said recovered part to deacidification, purification and separation to extract the alkylate(s); and
    (h) recycling to step (b) the acid-containing phase after said gas separation and a cooling, said recycled acid containing phase acting as said sulfuric acid composition, part of said acid-containing phase being withdrawn to regeneration prior to being recycled and being replaced by fresh acid.

2. The method of claim 1, wherein:
    steps (a), (b), (c) and (d) are run in vertical flows;
    steps (b) and (h) are controlled in such a manner that the amount of sulfuric acid circulating through the reaction chamber and having been processed in step (f) ranges between 40 to 80 m.sup.3/t of commercial grade alkylate (s);
    steps (b) and (d) are controlled in such a manner that in step (b), the first emulsion flows at a speed of 1.5 to 3.5 m/s and in step (d), the second emulsion flows in the reaction chamber at a speed of 2 to 4 m/s; and
    steps (c) and (d) are controlled in such a manner that the at least one olefin is injected with a pressure drop higher than 1 kg/cm$^2$.

3. The method of claim 1, wherein a further portion of said at least one olefin is injected into the reaction mixture at an outlet of the reaction chamber.

4. The method of claim 1, wherein said at least one isoparaffin comprises isobutane and said at least one olefin comprises propylene, butylenes, amylenes or mixtures thereof.

5. A method for separating into phases a reaction mixture exiting from an unit of sulfuric acid alkylation of at least one isoparaffin by at least one olefin, said phases including a liquid hydrocarbon-containing phase and a liquid acid-containing phase, which comprises the steps of:
    injecting said reaction mixture at a speed of 4 to 10 m/s into a hydrocylone in order to separate it into said liquid hydrocarbon-containing phase and said liquid acid-containing phase; and
    further processing said phases by subjecting each of said phase to a pressure reduction, injecting the phase having been subjected to said pressure reduction into a gas separator, recovering liquids from said gas separator by means of a pump for further utilization, and extracting vapors from said separator by means of a compressor.

6. The method of claim 5, wherein the phases having been subjected to said pressure reduction, are injected into separate gas separators.

7. The method of claim 5, wherein:
    the phases having been subjected to said pressure reduction, are injected into a same gas separator comprising a vessel divided by an overflow baffle plate into a settling tank and an accumulating tank, said baffle plate having an upper end;
    reaction products to be recovered are withdrawn from said accumulating tank and subjected to rectification in order to obtain a commercial grade alkylate;
    acid is withdrawn from a bottom part of the settling tank for recycling and regeneration; and
    other reaction products to be recycled are withdrawn from the settling tank at a level that is lower than the upper end of the overflow baffle plate.

8. The method of claim 5, wherein:
    the hydrocarbon-containing phase exiting from the hydrocyclone is injected into another hydrocyclone where it is separated into an upper lightweight flow and a lower heavy weight flow;
    the upper lightweight flow is subjected to pressure reduction and gas separation and then to rectification and fractionation in order to obtain a commercial grade alkylate; and
    the lower heavy weight flow is subjected to pressure reduction and gas separation and then recycled to the unit.

9. The method of claim 5, wherein:
    the acid-containing phase existing from the hydrocylone is injected into another hydrocyclone wherein it is separated into an upper lightweight flow and a lower heavy weight flow;
    the upper lightweight flow that is enriched by acid is returned to the unit as a first portion of acid to be recycled; and the lower heavy weight flow is separated into a first part that is returned to the unit as a second portion of acid to be recycled, and a second part that is discharged as waste acid for further regeneration.

10. The method of claim 9, wherein:

the lower heavy weight flow separated within the other hydrocyclone is injected into a further hydrocyclone where it is separated into another upper lightweight flow and another lower lightweight flow;

the other lower heavy weight flow obtained in said further hydrocyclone is used as said second portion of acid to be recycled; and the other upper lightweight flow obtained in said further hydrocyclone is discharged as further waste acid for further regeneration.

11. The method of claim 5, comprising the additional step of carrying out a gas separation downstream of the hydrocyclone.

12. A device for the production of alkylate(s) by sulfuric acid alkylation of at least one isoparaffin with at least one olefin, comprising:

(a) a mixing chamber for preparing a mixture of said at least one isoparaffin with recycled reaction products;

(b) an emulsion chamber for preparing a first hydrocarbons-in-sulfuric acid emulsion by mixing sulfuric acid with the mixture prepared in the mixing chamber (a);

(c) a pre-reaction chamber for preparing a second emulsion, where a given portion of said at least one olefin is injected in jet streams into the first hydrocarbons-in-sulfuric acid emulsion coming from the emulsion chamber (b); and (d) a reaction chamber of given height and cross-section where the second emulsion coming from the pre-reaction chamber (c) is injected through nozzles and another portion of the at least one olefin is injected in jet streams all over the cross-section and height of said reaction chamber; wherein said mixing chamber (a), emulsion chamber (b), pre-reaction chamber (c) and reaction chamber (d) are coaxially arranged one above the other in vertical position and altogether form a reactor with said mixing chamber (a) being located at the bottom of the reactor and said reaction chamber (d) on top thereof.

13. A device for separating a reaction mixture recovered from a unit of sulfuric acid alkylation of isoparaffins by olefins, in order to obtain a liquid acid-containing phase, a hydrocarbon-containing phase and a vapor phase, wherein said device comprises a horizontal vessel incorporating:

(a) at least one vertical overflow baffle plate that extends within said vessel and divides it into one settling tank and at least one accumulation tank;

(b) supply connecting pipes for introducing the reaction mixture into the settling tank;

(c) outlet connecting pipes for discharging the acid-containing phase from a bottom portion of the settling tank;

(d) other outlet connecting pipe for discharging the liquid hydrocarbon phase in the form of two separate flows, one of said flows being directed back to the unit for use as recycled reaction products, the other one of said flows consisting of commercial grade reaction products and being subjected to rectification and fractionation in order to obtain commercial grade alkylates, wherein the other outlet connecting pipe through which the other one of said flows exits from the vessel are located in a bottom portion of said at least one accumulation tank; and (e) at least one further outlet connecting pipe for discharging the vapor phase from an upper part of the vessel.

14. The device of claim 13 wherein the other outlet connecting pipe through which the one flow is discharged for use as recycled reaction products is in the form of a perforated pipe header extending in the settling tank at a given distance from the baffle plate, said pipe header having an axis parallel to the overflow baffle plate and extending upwards at a given height from the bottom portion of said settling tank.

15. The device of claim 14 wherein the height of said pipe header as measured from the bottom portion of the settling tank amounts to 0.5 to 0.8 times the height of the overflow baffle plate and the distance at which said pipe header extends from the baffle plate is 0.25 to 1.0 times the height of said baffle plate.

16. The device of claim 13. The device is provided with two of said at least one overflow baffle plate whereby two of said at least one accumulation tank are formed, one of said accumulation tanks being positioned on one side of the settling tank and collecting the commercial grade reaction products, the other one of said accumulation tank being positioned on an opposite side of the settling tank and being provided with an outlet connecting pipe for discharge of the reaction products to be recycled.

17. The device of claim 16, which comprises two of said at least one further outlet connecting pipes for vapor discharge, one of said further connecting pipe being positioned above the accumulating tank from which the commercial grade reaction products are extracted and the other one above the other accumulating tank from which the reaction products to be recycled are extracted.

18. The device of claim 16, wherein the settling tank comprises an additional vertical baffle plate that divides it into a settling section for recycled reaction products and a settling section for commercial grade reaction products, each of the said sections being provided with supply connecting pipes for corresponding flows of said liquid hydrocarbon containing phase.

19. The device of claim 18 wherein the additional baffle plate has a lower end that extends at a distance away from the bottom of the vessel and an upper end that extends at a height that is 30 to 100 mm higher than the upper end of the overflow baffle plates.

20. The device of claim 13, wherein supply connecting pipes are provided for introducing sulfuric acid in the settling section for the recycled reaction products, and an outlet connecting pipe located in the settling section for the commercial grade reaction products for discharging sulfuric acid from the same.

* * * * *